United States Patent [19]

Smith et al.

[11] Patent Number: 4,996,157
[45] Date of Patent: Feb. 26, 1991

[54] BIOLOGICAL CONTROL OF PHYTOPHTHORA BY TRICHODERMA

[75] Inventors: Victoria L. Smith; Wayne F. Wilcox; Gary E. Harman, all of Geneva, N.Y.

[73] Assignee: Cornell Research Foundation, Inc., Ithaca, N.Y.

[21] Appl. No.: 271,143

[22] Filed: Nov. 14, 1988

[51] Int. Cl.$^5$ .................... C12N 1/14; A01N 63/04
[52] U.S. Cl. .................... 435/254; 435/911; 424/93
[58] Field of Search .................... 435/945, 911; 47/58; 71/3, 65, 77; 424/93

[56] References Cited

U.S. PATENT DOCUMENTS 4,489,161  12/1984  Papavizas .................... 435/254

OTHER PUBLICATIONS

Lumsden, R. D., et al, Phytopathology, vol. 79, No. 3, 361–366 (1989).
Wilton, J. H., et al, Phytopathology, vol. 72, No. 7, 1010–1011 (1982).
Abd–El Moity (1982) Phytopathology 72:396–400.
Chet, et al. (1981) Phytopathology 71:286–290.
Hoitinak, et al. (1986) Ann. Rev. Phytopath 24:93–114.
Ellis; et al. (1986) Plant Disease 70:24–26.
Nelson, et al. (1983) Phytopathology 73:1457–1462.
Orlikowski, et al. (1985) Nachrichtenbl. Deut. Pflanzenshutzd. (Braunschweig) 37:78–79.
Jeffers et al, 1982, Phytopathology, 72:533–528.
Wilcox, in 1987 New York State Pesticide Recommendations. Cornell University, Ithaca, New York 533 pages.
Abd–El Moity et al, 1982, Phytopathology, 72:396–400.
Ebd–El Moity et al, 1981, Phytopath. Z., 100:29–35.
Ohr et al, 1973, Phytopathhology, 63:965–973.
Chet et al, 1981, Phytopathology, 71:286–290.
Elad et al, 1982, Plant & Soil, 66:279–281.
Ruppel et al, 1983, Crop Protection, 2:399–408.
Jordan et al, 1978, Ann. Appl. Biol., 89:139–141.
Marois et al, 1982, Plant Dis., 66:1166–1168.
Chet et al, 1981, Microb. Ecol., 7:29–38.
Hadar et al, 1984, Phytopathology, 74:106–110.
Harman et al, 1983, Seed Sci. & Technol., 11:893–906.
Sivan et al, 1984, Phytopathology, 74:498–501.
Papavizas, 1985, Ann. Rev. Phytopathol., 23:23–54.
Hoitink et al, 1986, Ann. Rev. Phytopathol., 24:93–114.
Ellis et al, 1986, Plant Disease, 70:24–26.
Nelson et al, 1983, Phytopathology, 73:1457–1462.
Kraft et al, 1983, Plant Dis., 67:1234–1237.

Primary Examiner—Elizabeth C. Weimar
Assistant Examiner—Che Swyden Chereskin

[57] ABSTRACT

Certain strains of Trichoderma and Gliocladium protect plants against plant diseases caused by Phytophthora spp., for example crown and collar rot. The Trichoderma or Gliocladium are applied to the root system biosphere of the plant.

5 Claims, No Drawings

BIOLOGICAL CONTROL OF PHYTOPHTHORA BY TRICHODERMA

This invention was made in part with Government support under Grant No. USDA 87-CRSR-22992, awarded by the United states Department of Agriculture. The Government has certain rights in the invention.

BACKGROUND OF THE INVENTION

Crown and collar rot, caused by at least four Phytophthora spp. (Jeffers et al, 1982, *Phytopathology*, 72:533-538) is a widespread and economically serious problem of apples throughout the Northeast U.S. In New York State, this disease appears to be the most common biological cause of premature tree decline and death, and in Pennsylvania, many growers have abandoned the horticulturally-desirable MM 106 rootstock because of high crown rot incidence or its perceived threat. Because no single approach to the control of Phytophthora crown rot has proved reliable, growers have been advised to adopt an integrated or additive disease management strategy, utilizing a combination of site selection, site modification, rootstock selection, and chemical treatments where appropriate (Wilcox, In: 1987 New York State Pesticide Recommendations. Cornell University, Ithaca, N.Y. 533 pp). However, the possibility of introducing a biological control agent as an additional component of such a program has heretofore been largely ignored.

Species of Trichoderma and Gliocladium have been shown to provide varying levels of biological control of a number of important soil-borne plant pathogens, including *Sclerotium cepivorum* (Abd-el Moity et al, 1982, *Phytopathology*, 72:396-400; Abd-el Moity et al, 1981, *Phytopath. Z.*, 100:29-35), *Armillaria mellea* (Ohr et al, 1973, *Phytopathology*, 63:965-973), *Rhizoctonia solani* (Chet et al, 1981, *Phytopathology*, 71:286-290; Elad et al, 1982, *Plant and Soil*, 66:279-281; Ruppel et al, 1983, *Crop Protect.*, 2:399-408), *Verticillium dahliae* (Jordan et al, 1978, *Ann. Appl. Biol.*, 89:139-141; Marios et al, 1982, *Plant Dis.*, 66:1166-1168) and *Pythium spp*. (Chet et al, 1981, *Microb. Ecol.*, 7:29-38; Hadar et al, 1984, *Phytopathology*, 74:106-110; Harman et al, 1983, *Seed Sci. & Technol.*, 11:893-906; Sivan et al, 1984, *Phytopathology*, 74:498-501). While there have been many recent advances in the use of Trichoderma spp. as biological control agents (Papavizas, 1985, *Ann. Rev. Phytopathol.*, 23:23-54), to date there have been no concerted efforts made to use these fungi to control diseases caused by soil-borne Phytophthora spp., the economic importance of such diseases and the close relationship of the Phytophthora and Pythium genera notwithstanding.

Despite the lack of direct evidence, there exists correlative evidence that certain Trichoderma spp. may be involved in the biological control of several diseases caused by Phytophthora spp., e.g., *T. viride* versus heart rot of pineapple caused by *P. parasitica* (Papazivas, 1985, suora). More compelling correlative evidence is supplied by the well-documented ability of composted hardwood bark (CHB) to provide control of Phytophthora disease of woody plants when incorporated into their rhizospheres (Hoitinak et al, 1986, *Ann. Rev. Phytopathol.*, 24:93-114), including control of crown rot of apple under field conditions (Ellis et al, 1986, *Plant Dis.*, 70:24-26), and the related documentation that the addition of CHB to a container potting mix resulted in a 100 to 100,000 fold increase in the population levels of *T. harzianum* in this rooting medium (Nelson et al, 1983, *Phytopathology*, 73:1457-1462).

It has been recently pointed out that the potential of Trichoderma spp. for use as biological control agents has been studied primarily as an end in itself rather than as a synergistic or additive component in a broader integrated pest management system (Papavizas, 1985, supra). Nevertheless, there are several studies in which such an approach has been attempted successfully, e.g., methyl bromide plus Trichoderma for the control of *Armillaria mellea* (Ohr, 1973, supra), and *T. harzianum* plus PCNB for the control of root rot and damping off of pea caused by *Pythium ultimum* (Kraft et al, 1983, *Plant Dis.*, 67:1234-1237).

DESCRIPTION OF THE INVENTION

This invention relates to novel strains of Trichoderma and Gliocladium spp. which are useful in controlling plant diseases caused by Phytophthora spp. such as root rot, crown and collar rot, Aphanomyces root rot and the method for their use.

The Trichoderma and Gliocladium species of the invention are applied to the biosphere of the root system of the plant to be protected in an amount sufficient to colonize and populate the plant root system biosphere, thereby controlling (i.e. reducing the incidence or severity of or eliminating) Phytophthora spp. caused plant diseases.

A sufficient inoculum typically should provide between $10^4$ to $10^6$ colony-forming-units of Trichoderma and Gliocladium per gram of soil to assure establishment of the beneficial Trichoderma and Gliocladium in the plant root biosphere. Depending on the climate conditions, soil conditions, the amount of Phytophthora spp. present in the biosphere, and the possible presence of other competing microorganisms in the biosphere being inoculated, lesser or greater amounts of Trichoderma or Gliocladium can be used to establish the Trichoderma or Gliocladium of the invention in the plant biosphere.

Preferably, the Trichoderma or Gliocladium is added to the plant biosphere in the form of a preformed inoculum comprising a carrier on which the Trichoderma or Gliocladium has been colonized and if desired, water and/or nutrients or trace minerals which assist the growth of the Trichoderma or Gliocladium. Carriers such as peat and/or wheat bran, vermiculite, pasteurized soil and the like can be employed. The inoculum is prepared by mixing the carrier and Trichoderma or Gliocladium, usually with water, and any other desired adjuvants, in amounts to cause colonization of the Trichoderma or Gliocladium on the carrier. The mixture is then incubated until the Trichoderma or Gliocladium is soundly established on the carrier so as it, in turn, provides a suitable vehicle for colonizing the Trichoderma or Gliocladium in the soil biosphere to which the inoculum is subsequently added.

The Trichoderma or Gliocladium containing inoculum or other compositions containing the Trichoderma or Gliocladium can be applied by means known in the art, depending on its physical state.

EXAMPLES

Materials and Methods

Sample collection: Soil was collected from orchards in Orleans County, New York on 5 June 1987. Samples were collected from around the crowns of apple and cherry trees growing on heavy, wet, and/or frequently-flooded soil; trees were asymptomatic for Phytophthora root and crown rot. Samples were decimally diluted in sterile distilled water and plated on a medium selective for Trichoderma spp. (TSM, 5). Isolates of candidate biocontrol fungi were collected from the plates by mass transfer of conidia after 5 days incubation on the lab bench. Isolates were identified to species using Rifai's key (Rifai, 1969, *Mycol. Pap.*, 116:1–56).

Soil also was collected from fields in Livingston County, New York, on 16 November 1987. Samples were taken from fields reported to be suppressive to Aphanomyces root rot of pea. Individual soil cores were taken along an arbitrary transect through the field; cores from a particular field were bulked and thoroughly mixed. Samples were decimally diluted in sterile distilled water and plated on TSM. Isolates were collected and identified as outlined above.

Soil also was collected from a wet grassy area on Cornell University's Vegetable Research Farm located in Geneva, Ontario County, N.Y. Soil samples were diluted as outlined above and plated on TSM. Plates were incubated at 11° C.

In vitro interactions with Phytophthora spp: Candidate isolates were paired with *P. cactorum* and *P. cambivora* on corn meal agar and incubated at 10°, 16° and 22° C. Cultures were observed daily and any overgrowth of Phytophthora by Trichoderma was noted. Any antibiotic activity of Trichoderma against Phytophthora was noted. Antibiotic activity was defined as any inhibition of radial growth of Phytophthora by Trichoderma.

Greenhouse screen: Candidate isolates that were able to grow well at low temperature (10°–11° C.) and exhibited antibiotic activity against Phytophthora were chosen for further evaluation in the greenhouse.

Preparation of soil: soil was prepared by mixing 4 l pasteurized soil, 8 l vermiculite, and 2 l water. All ingredients were placed in a large plastic bag and thoroughly mixed.

Preparation of Trichoderma inoculum: a mixture of peat and wheat bran (1:1 v/v; moistened with 1 part distilled water) was autoclaved twice, on two successive days, 15 min each at 15 lbs pressure. After thorough cooling, the peat-bran preparation was inoculated with 4–6 disks, each 5 mm diameter, cut from the actively-growing margin of a colony of the candidate isolate growing on corn meal agar (Difco). Peat-bran inoculum was incubated on the lab bench for 7 to 10 days. Inoculum of candidate isolates was thoroughly mixed both alone and in combination with soil infested with *P. cactorum*, at a rate of ~20 ml/3.25 l soil, resulting in $10^4$ to $10^6$ colony-forming-units of the candidate isolate per gram of soil mix.

Preparation of Phytophthora inoculum: a mixture of V8 juice broth and vermiculite (3:5 v/v; V8 broth=200 ml V8 juice, 800 ml distilled water, and 2 grams $CaCO_3$/l) was autoclaved twice, on two successive days, 15 min. each at 15 lbs pressure. After thorough cooling, the V8-vermiculite preparation was inoculated with 4–6 disks, each 5 mm diameter, cut from the actively-growing margin of a colony of *P. cactorum* growing on corn meal agar. V8-vermiculite was incubated on the lab bench for 2 to 3 wk. V8-vermiculite then was placed on 4 layers of cheesecloth and washed free of V8 juice. The preparation consisted primarily of oospores and sporangia in a vermiculite carrier. Inoculum was thoroughly mixed into soil at a rate of 250 ml/12 l soil.

After addition of al inocula, soil was allowed to stand at room temperature for at least 12 hr, but not more than 24 hr, prior to use.

Five sprouted seeds from open-pollinated McIntosh apples were planted per pot, and each Trichoderma X Phytophthora combination was replicated five times. Immediately prior to potting, a sample (~15 grams fresh weight) was taken from each soil lot and ten-gram subsamples were decimally diluted and plated on TSM (Davet, 1979, *Annales de Phytopathologie.*, 11:529–533). Initial levels of Trichoderma were estimated after five days incubation at room temperature.

Pots containing seedlings were placed in a greenhouse maintained at 18° C. After 2 weeks pots containing seedlings were flooded to a depth of 1 cm for 72 hr, to induce zoospore production and subsequent infection by Phytophthora. During flooding, leaf disk baits were used to estimate relative levels of Phytophthora in each pot (Wilcox et al, 1985, *Phytopathology*, 75:648–653). Seven to 10 days after conclusion of flooding, plants in each pot were evaluated for the number of hypocotyl lesions, percent root rot, and total plant weight.

Data analysis: Presence of Phytophthora and Trichoderma were treated as qualitative variables in analysis of variance, with plant weight as the independent variable. Correlation coefficients between all variables (number of leaf disk baits colonized, number of hypocotyl lesions, percent root rot, total plant weight, and initial CFU Trichoderma) were calculated.

Results

Approximately 67 strains initially were screened in vitro. Of these, 27 showed sufficient antibiotic activity to be tested in the greenhouse. Of those tested in the greenhouse, 3 gave moderate protection against Phytophthora and 7 were very effective in reducing damage by *P. cactorum* (Table 1). Data on these strains is given in Table 2. For plants grown in the presence of Trichoderma alone, there was a significant increase in the total plant weight, compared to plants grown in potting medium without Trichoderma. For plants in the Trichoderma X Phytophthora combinations, total plant weight was increased and percent root rot was less than for plants in the presence of Phytophthora alone (Table 2).

TABLE 1

Selection of isolates effective against Phytophthora spp.

| Source of isolates | Total number of isolates | Effective in vitro | Effective in planta |
|---|---|---|---|
| Cornell Vegetable Farms | 23 | 10 | 4 |
| Orleans Co., New York | 30 | 6 | 2 |
| Livingston Co., New York | 14 | 11 | 4 |

TABLE 2

Efficacy of strains of Trichoderma against Phytophthora spp.

| treatment | total plant weight (gm) | percent change[a] | root rot rating |
|---|---|---|---|
| Isolates from orchard soils | | | |
| *P. cambivora* | 3.54 | — | 2.2 |
| *P. cactorum* | 3.48 | — | 2.8 |
| *T. harzianum* Rifai #30 | 3.74 | 7.5 | 2.0 |

TABLE 2-continued

Efficacy of strains of Trichoderma against Phytophthora spp.

| treatment | total plant weight (gm) | percent change[a] | root rot rating |
|---|---|---|---|
| (ATCC 20902)[b] X P. cactorum | | | |
| *Isolates from the Vegetable Research Farm* | | | |
| P. cambivora | 1.47 | — | 3.4 |
| P. cactorum | 1.86 | — | 3.4 |
| Trichoderma viride Pers. ex S.F. Gray #14X (ATCC 20898) P. cambivora | 3.27 | 122.45 | 1.8 |
| Trichoderma koninoii Oud. #23X (ATCC 20899) P. cambivora | 1.69 | 14.97 | 3.8 |
| T. viride #24X (ATCC 20900) P. cambivora | 3.49 | 137.41 | 1.6 |
| T. koningii #25X (ATCC 20901) P. cambivora | 2.07 | 40.82 | 2.8 |
| Trichoderma viride Pers. ex S.F. Gray #14X (ATCC 20898) P. cactorum | 2.23 | 19.89 | 2.8 |
| Trichoderma koningii Oud. #23X (ATCC 20899)[b] P. cactorum | 3.40 | 82.80 | 2.6 |
| T. viride #24X (ATCC 20900) P. cactorum | 2.03 | 9.14 | 3.8 |
| T. koningii #25X (ATCC 20901) P. cactorum | 3.71 | 99.46 | 2.0 |
| *Isolates from Aphanomyces-suppressive soils* | | | |
| P. cactorum | 3.31 | — | 1.9 |
| Gliocladium virens Miller, Giddens & Foster #31X (ATCC 20903) P. cactorum | 4.47 | 35.0 | 1.3 |
| G. virens #35X (ATCC 20904) P. cactorum | 3.77 | 13.9 | 2.0 |
| T. viride #36X (ATCC 20905) P. cactorum | 4.05 | 22.36 | 1.7 |
| G. virens #41X (ATCC 20906) P. cactorum | 3.50 | 5.74 | 1.5 |
| T. harzianum #43X (ATCC 20907) P. cactorum | 3.38 | 2.11 | 1.7 |

[a] percent change over Phytophthora alone treatments.
[b] each of the Trichoderma spp. indicated by ATCC No. in this table are deposited at the American Type Culture Collection, Rockville, MD under that number to meet the requirements of the Budapest Treaty on the International Recognition of the Deposit of Microorganisms for the Purposes of Patent Procedure.

Discussion

The ten isolates noted in Table 2 have activity against *Phytophthora cactorum*, both in vitro and in planta. These are the first Trichoderma found with activity against this genus of pathogenic fungi. The isolates also were tested for tolerance to the fungicide metalaxyl in vitro. Radial growth on corn meal agar amended with fungicide was not affected at concentrations as high as 10 ug/l. The results of this study indicate that these isolates of Trichoderma are useful in an integrated program to manage *P. cactorum* on susceptible trees.

We claim:

1. A biocontrol agent effective against *Phytophthora cactorum* selected from the group consisting of:
   Gliocladium virens, 031 (ATCC 20903);
   Gliocladium virens, 035 (ATCC 20904); and
   Gliocladium virens, 041 (ATCC 20906).

2. The biocontrol agent of claim 1 which is *Gliocladium virens*, 031 (ATCC 20903).

3. The biocontrol agent of claim 1 which is *Gliocladium virens*, 035 (ATCC 20904).

4. The biocontrol agent of claim 1 which is *Gliocladium virens*, 041 (ATCC 20906).

5. A method of controlling *Phytophthora cactorum* caused plant diseased which comprises applying to the plant root biosphere of the plant to be protected a biosphere colonizing amount of a biocontrol agent selected from the group consisting of:
   Gliocladium virens, 031 (ATCC 20903);
   Gliocladium virens, 035 (ATCC 20904); and
   Gliocladium virens, 041 (ATCC 20906).

* * * * *

UNITED STATES PATENT AND TRADEMARK OFFICE
CERTIFICATE OF CORRECTION

PATENT NO. : 4,996,157

DATED : February 26, 1991

INVENTOR(S) : Victoria L. Smith et al

It is certified that error appears in the above-identified patent and that said Letters Patent is hereby corrected as shown below:

Title page

Change the title to --BIOLOGICAL CONTROL OF PHYTOPHTHORA BY TRICHODERMA AND GLIOCLADIUM--.

Claim 5 (column 6, line 43), change "diseased" to --diseases--

Signed and Sealed this

Twenty-ninth Day of December, 1992

Attest:

DOUGLAS B. COMER

*Attesting Officer*   Acting Commissioner of Patents and Trademarks